US010568985B2

(12) United States Patent
Runge et al.

(10) Patent No.: US 10,568,985 B2
(45) Date of Patent: Feb. 25, 2020

(54) PHOTODEGRADABLE POLYCAPROLACTONE FUMARATE BLOCK COPOLYMERS

(71) Applicants: Michael Brett Runge, Pine Island, MN (US); Michael J. Yaszemski, Rochester, MN (US)

(72) Inventors: Michael Brett Runge, Pine Island, MN (US); Michael J. Yaszemski, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 13/955,279

(22) Filed: Jul. 31, 2013

(65) Prior Publication Data
US 2014/0039075 A1    Feb. 6, 2014

Related U.S. Application Data

(60) Provisional application No. 61/678,290, filed on Aug. 1, 2012.

(51) Int. Cl.
| A61L 27/18 | (2006.01) |
| C08L 67/04 | (2006.01) |
| C08G 63/08 | (2006.01) |
| A61L 27/56 | (2006.01) |

(52) U.S. Cl.
CPC .......... *A61L 27/18* (2013.01); *C08G 63/08* (2013.01); *C08L 67/04* (2013.01); *A61L 27/56* (2013.01); *A61L 2430/32* (2013.01)

(58) Field of Classification Search
CPC .................. C08L 67/04; C08G 63/08
See application file for complete search history.

(56) References Cited

U.S. PATENT DOCUMENTS

| 4,176,145 | A | 11/1979 | Guillet |
| 5,352,716 | A | 10/1994 | Chapman et al. |
| 5,763,518 | A | 6/1998 | Gnatowski et al. |
| 7,816,461 | B2 | 10/2010 | Wang et al. |
| 2005/0245638 | A1 | 11/2005 | Mezza |
| 2006/0002978 | A1 | 1/2006 | Shea et al. |
| 2007/0043202 | A1 | 2/2007 | Yaszemski et al. |
| 2007/0155926 | A1 | 7/2007 | Matyjaszewski et al. |

(Continued)

OTHER PUBLICATIONS

Runge et al (Development of Photo Degradable Polycaprolactone Fumarate Block Copolymers, Polymer Preprints 2012, 53(1), 291).*

(Continued)

*Primary Examiner* — Rachel Kahn
(74) *Attorney, Agent, or Firm* — Quarles & Brady LLP (57) ABSTRACT

A polycaprolactone fumarate copolymer useful as a material for a biocompatible scaffold for tissue engineering applications is disclosed. The copolymer includes at least one caprolactone unit, at least one fumarate unit, and at least one third unit selected from the group consisting of acrylate units and styrenic units. A linking moiety forms a link between the third unit and at least one caprolactone unit or at least one fumarate unit. The linking moiety can be photodegradable. In one form, the third unit includes at least one methyl methacrylate unit. The copolymer can be used to form the wall of a nerve conduit.

14 Claims, 8 Drawing Sheets

(56) References Cited

U.S. PATENT DOCUMENTS

| | | |
|---|---|---|
| 2008/0194792 A1 | 8/2008 | Wang et al. |
| 2009/0110732 A1 | 4/2009 | Jabbari |
| 2009/0259016 A1 | 10/2009 | Johnson et al. |
| 2011/0245852 A1 | 10/2011 | Downes et al. |
| 2011/0276066 A1 | 11/2011 | Pandit et al. |
| 2013/0331869 A1 | 12/2013 | Runge et al. |

OTHER PUBLICATIONS

Priftis et al (Miktoarm Star Copolymers of Poly($\varepsilon$-Caprolactone) from a Novel Heterofunctional Initiator, Journal of Polymer Science: Part A: Polymer Chemistry, vol. 45, 5164-5181 (2007)).*

Turunen et al (Synthesis, characterization and crosslinking of functional star-shaped poly($\varepsilon$-caprolactone), Polymer International, 51:92-100 (2001)).*

Kaiser et al (Norrish Type I Cleavage of Aliphatic Carboxylic Acids and Esters in Solution. A CIDNP.-study, Helvetica Chimica Acta, vol. 62, Issue 5, pp. 1475-1484, 1979).*

Alexander R. Nectow et al., "Biomaterials for the Development of Peripheral Nerve Guidance Conduits", Tissue Engineering: Part B, pp. 1-11 (Aug. 3, 2011).

Rodriguez et al., "Highly permeable polylactide-caprolactone nerve guides enhance peripheral nerve regeneration through long gaps", Biomaterials 1999, 20, 1489-500.

Cai et al., "Permeable guidance channels containing microfilament scaffolds enhance axon growth and maturation", J Biomed Mater Res A 2005, 75, 374-86.

Chang et al., "Highly Permeable Genipin-Cross-linked Gelatin Conduits Enhance Peripheral Nerve Regeneration", Artif Organs 2009, 33, 1075-85.

Vleggeert-Lankamp et al., "Pores in synthetic nerve conduits are beneficial to regeneration", J Biomed Mater Res A 2007, 80, 965-82.

A Brief Guide to Polymer Nomenclature; IUPAC (2012).

* cited by examiner

PHOTODEGRADABLE POLYCAPROLACTONE FUMARATE BLOCK COPOLYMERS

CROSS-REFERENCES TO RELATED APPLICATIONS

This application claims priority from U.S. Patent Application No. 61/678,290 filed Aug. 1, 2012.

STATEMENT REGARDING FEDERALLY SPONSORED RESEARCH

This invention was made with government support under NIH AR056950 and NIH NS066851 awarded by National Institutes of Health. The government has certain rights in the invention.

BACKGROUND OF THE INVENTION

1. Field of the Invention

This invention relates to the synthesis of a polycaprolactone fumarate copolymer useful as a material for a biocompatible scaffold for tissue engineering.

2. Description of the Related Art

Segmental nerve injuries are quite common, and the autologous nerve graft remains the gold standard in the field of peripheral nerve surgery. However, due to lack of availability of autologous nervous tissue, alternative structures have been proposed for use in the treatment of nerve defects.

Synthetic guidance conduits can be used for nerve defects of less than three centimeters. Available synthetic nerve conduits include: polyglycolic acid (PGA) conduits (e.g., Neurotube™ conduit); polylactide-co-caprolactone (PLCL) conduits (e.g., Neurolac™ conduit); collagen conduits (e.g., Neurogen™ and Neuromatrix™ conduits) and polyvinyl alcohol (PVA) conduits (e.g., SaluBridge™ conduit). Nerve guidance conduits are mainly non-permeable which limits the flux of molecules through polymer, and the flux varies between molecules and polymers. Non-permeable conduits limit the exchange of nutrients and cellular waste within the conduit, and repair of longer defects may require enhanced conduit permeability.

Even though nerve conduits can be used to repair segmental nerve defects, defects larger than three centimeters are challenging. It has become increasingly believed that porous nerve conduit walls enhance regeneration. Porous nerve conduits are reported in the literature. Example porous nerve conduit materials include: (i) high permeability polycaprolactone (see Rodriguez et al., *Biomaterials* 1999, 20, 1489-500); (ii) low permeability polycaprolactone (see Rodriguez et al., *Biomaterials* 1999, 20, 1489-500); (iii) porous poly(lactic-co-glycolic acid) (see Cai et al., *J Biomed Mater Res A* 2005, 75, 374-86); and (iv) porous gelatin (see Chang et al., *Artif Organs* 2009, 33, 1075-85). Nonporous, macroporous, and microporous scaffolds have also been reported in Vleggeert-Lankamp et al., *J Biomed Mater Res A* 2007, 80, 965-82, and for a six millimeter defect, the best scaffold was microporous, and 60% possessed nerve cable. However, both microporous and macroporous scaffolds had fibrous tissue infiltration which is a disadvantage.

Techniques for creating porous nerve conduit structures have been limited to porogen leaching techniques which result in microporosity, typically five microns and larger. Not only are the pores larger than five microns (and many times tens to hundreds of microns), the pores are also random which allows fibrous tissue infiltration and uncontrolled diffusion of all molecules through the porous walls. Also, high porosity is required (>80% porosity) to reach interconnected porosity resulting in compromised mechanical properties. Thus, existing porous nerve conduit structures exhibit one or more of the following problems: fibrous tissue infiltration, uncontrolled diffusion of all molecules through the porous walls, and compromised mechanical properties.

Nanoporous materials have numerous applications in nonmedical industries for uses such as membranes, surface patterning, and templates for inorganic materials. These applications have typically used block copolymer (e.g., an A-B block copolymer) self-assembly wherein the block copolymers assemble by phase separation of A and B blocks to form nanostructures. Although these types of nanomaterials are widely used in other industries, they have yet to find a robust approach for incorporation into the biomaterials field.

Polycaprolactone fumarate (PCLF) is a cross-linkable derivative of polycaprolactone (PCL) that has been shown to be promising material for tissue engineering applications involving both the repair of segmental nerve defects as well as a bone substitute. PCLF also has potential as a drug delivery vehicle. PCLF has been used for the production of nerve conduits to repair segmental nerve defects. These PCLF nerve conduits have been shown to support robust nerve regeneration across the one centimeter rat sciatic nerve defect model and have warranted future clinical studies.

What is needed therefore is an improved biocompatible polycaprolactone fumarate formulation that can be used to manufacture a nerve conduit that does not allow for fibrous tissue infiltration, that controls diffusion of molecules through the nerve conduit wall, and that has acceptable mechanical properties.

SUMMARY OF THE INVENTION

To overcome the limitations of prior nerve conduit materials, we have developed nanoporous biomaterials through block copolymer assembly and chemo-selective degradation. The challenge, and what separates the nanoporous biomaterial approach of the invention compared to the previous applications is that we have the biodegradable material remain as the nanoporous scaffold, where previous applications have typically degraded the degradable polymer block, leaving behind a nondegradable polymer scaffold.

Photodegradable polymers are of significant interest in the field of biomaterials because the degradation can be initiated by exposure to ultraviolet (UV) light and provides an alternative mechanism to hydrolysis. We report herein our work developing nanoporous biodegradable biomaterials through block copolymer assembly and photolytic degradation. We have developed a block copolymer system comprising polycaprolactone fumarate-b-poly(methyl methacrylate) (PCLF-b-PMMA) linked via a photodegradable initiator. We report the synthesis of novel PCLF-b-PMMA branched block copolymers, and demonstrate that these block copolymers assemble into ordered nanomaterials in the solid state. After assembly, we show that these polymeric scaffolds can be selectively degraded by UV exposure. The UV degradation does not degrade the PCLF, but breaks the covalent bond between PCLF and PMMA and allows for selective removal of the poly(methyl methacrylate) (PMMA). This work describes a new approach to creating nanoporous biomaterials.

Alternative degradation mechanisms to simple hydrolysis in response to deliverable stimuli are of increasing interest for biomaterial applications because stimuli, for example light, can be used on command to degrade polymeric structures, change the macroscopic architecture of a scaffold, delivery therapeutic agents, or change the surface chemistry of the scaffold. Herein we disclose the following: (1) development of a novel photodegradable initiator for the synthesis of PCLF block copolymers wherein the photodegradable initiator acts as a linkage between the PCLF and secondary polymer block, upon exposure to UV light the linkage degrades and separates the two polymer chains, without degrading the individual polymer chains themselves; and (2) the synthesis of a photodegradable PCLF block copolymer comprising a PCLF block and a poly(methyl methacrylate) (PMMA) block. We have shown that these polymers can be degraded in solution by exposure to UV light. Although we have used PMMA as an illustrative example, any polyacrylate can be used with this specific initiator.

We have developed a block copolymer approach whereby the A-B block copolymer is connected via a photodegradable linkage. After assembly into a nanostructure, the individual polymer chains can be separated by exposure to UV light. At this point, the unwanted block can be washed away, and the biodegradable nanoporous structure remains.

Nanoporous scaffolds offer advantages over microporous scaffolds for various reasons. For example, cells are 2-3 orders of magnitude larger and cannot migrate through the nanoporous scaffold, and the nanopores are on the correct order of magnitude to control and be selective based on molecular size of diffusing molecules through the pores. Further selectivity may be enhanced by functionalizing the pore with proteins, similar in structure to nucleoporins. In addition, nanomaterials that possess interconnected porosity range in % porosity from approximately 21-37% porous, this gives the advantage that the mechanical integrity and strength of the scaffold is maintained.

Currently available synthetic conduits are merely a tube connecting proximal and distal nerve stumps. The present invention facilitates advancements in nerve conduit design such as growth factor delivery, nanofiber guidance of cell processes, increased nutrient availability, and electrically conductive conduits for stimulation.

These and other features, aspects, and advantages of the present invention will become better understood upon consideration of the following detailed description, drawings, and appended claims.

DETAILED DESCRIPTION OF THE INVENTION

Figure 1:
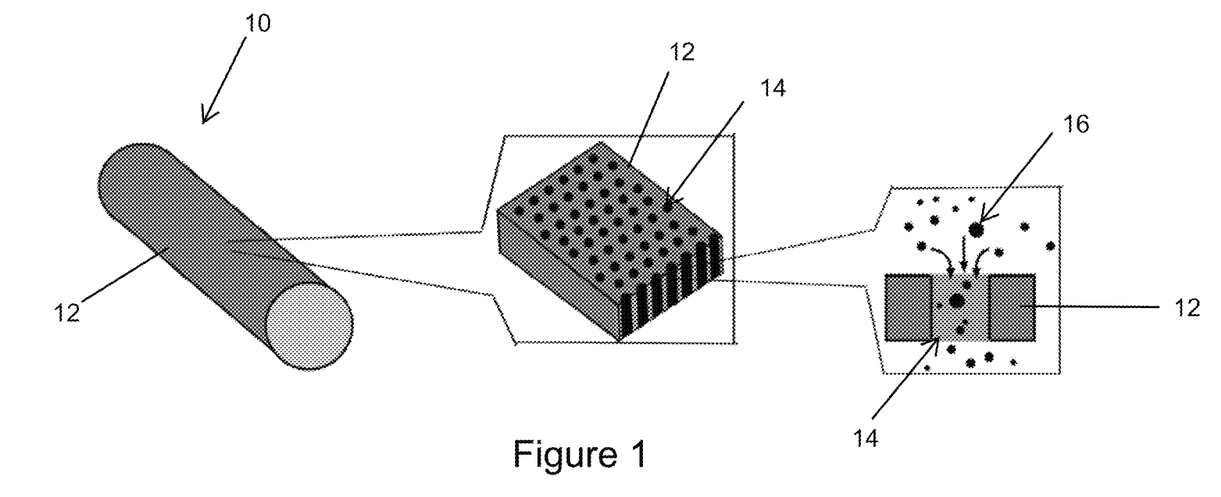
FIG. 1 shows one embodiment of a nerve conduit according to the invention.

Looking at FIG. 1, there is shown a nerve conduit 10 having a tubular biodegradable wall 12 with hollow channels 14. The channels 14 can have an average transverse diameter in a range from 1 to 500 nanometers, or in a range from 5 to 250 nanometers, or in a range from 10 to 100 nanometers. The wall 12 can have a porosity in a range of about 1% to about 50%, in a range of about 20% to about 40%, or in a range of about 20% to about 35%.

The nanoporosity provided by the channels 14 has many advantages. For example, nanoporosity allows nutrient and waste exchange between a nerve repair site and the adjacent outer environment. The nanoporosity prevents fibrous tissue infiltration through conduit wall 12. The nanoporosity may provide a route to future control of diffusion by differences in molecules 16 hydrodynamic radii. Optionally, functionalizing the pores with proteins can further control diffusion.

Figure 2:
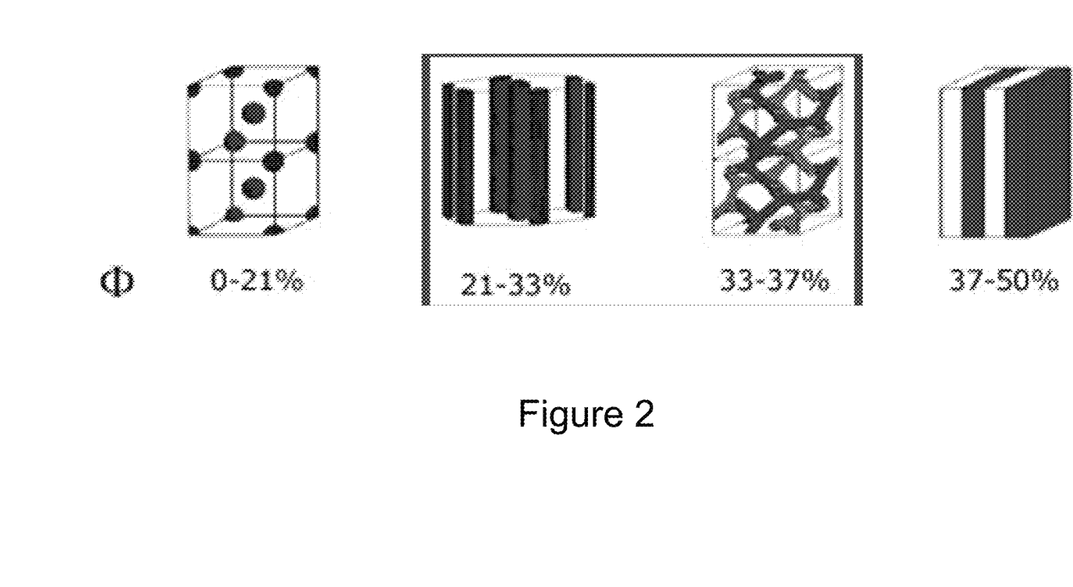
FIG. 2 shows example nanostructures formed from block copolymers of the invention.

Referring now to FIG. 2, accessing ten to one hundred nanometer structures can be difficult and numerous tools are not available that allow physical manipulation at a nanometer size scale. Block copolymer assembly is one method that can be used for nanomaterial fabrication. Various nanoporous structures (such as wall 12 in FIG. 1) are shown in FIG. 2 with porosities in the ranges of 0-21%, 21-33% (cylindrical), 33-37% (gyroidal), and 37-50%. Nanostructure block copolymers of the invention can assemble into the structures of FIG. 2.

The invention provides a biocompatible, biodegradable copolymer suitable for use in wall 12 of the nerve conduit 10 to achieve a nanoporous structure with desired porosity levels. The biocompatible, biodegradable copolymer includes at least one caprolactone unit as follows:

and at least one fumarate unit as follows:

and at least one third unit selected from the group consisting of acrylate units and styrenic units. In one embodiment, the third unit is a methyl methacrylate unit as follows:

In one form of the copolymer, at least one caprolactone unit and at least one fumarate unit form a main chain of the copolymer, and the third unit forms a side chain of the copolymer. In another form, the copolymer includes a first block in the main chain, and the first block has at least one caprolactone unit and/or at least one fumarate unit; and the copolymer includes a second block in the main chain, and the second block has at least one caprolactone unit and/or at least one fumarate unit.

A photodegradable linking moiety forms a link between the third unit and at least one caprolactone unit or at least one fumarate unit. In one form, the linking moiety links the first block and the second block in the main chain. In one non-limiting example, the linking moiety comprises an alkanoyl group or an alkanedioyl group. In another non-limiting example, the linking moiety comprises a dioxyalkyl group that links the first block and the second block. In another non-limiting example, the linking moiety comprises a benzyl group. In another non-limiting example, the linking moiety comprises a carbonyl group. In another non-limiting example, the linking moiety comprises a trivalent radical of a [(halo-alkylalkanoyl)oxy]-nitrobenzyl dihydroxyalkyl alkanedioate. In another non-limiting example, the linking moiety comprises a trivalent radical of (5-[(2-bromo-2-methylpropanoyl)oxy]-2-nitrobenzyl dihydroxypropyl butanedioate).

In one form, the copolymer has a number average molecular weight in the range of 3000 to 60,000 g mol$^{-1}$, or in the range of 5000 to 25,000 g mol$^{-1}$, or in the range of 10,000 to 20,000 g mol$^{-1}$. The copolymer may have a polydispersity index in the range of 1 to 6.

The invention provides another biocompatible, biodegradable copolymer suitable for use in wall 12 of the nerve conduit 10 to achieve a nanoporous structure with desired porosity levels. The biocompatible, biodegradable copolymer includes at least one caprolactone unit, at least one fumarate unit, and a linking moiety that links (i) at least one caprolactone unit and at least one fumarate unit, or (ii) at least one caprolactone unit and at least one caprolactone unit, or (iii) at least one fumarate unit and at least one fumarate unit. The linking moiety can include a carboxylic acid group. The linking moiety can be a bivalent radical of a dihydroxyalkyl ester of alkane-dicarboxylic acid. The linking moiety can be a bivalent radical of a dihydroxypropyl ester of butane-dicarboxylic acid. In one form, the copolymer has a number average molecular weight in the range of 3000 to 60,000 g mol$^{-1}$, or in the range of 5000 to 25,000 g mol$^{-1}$, or in the range of 10,000 to 20,000 g mol$^{-1}$. The copolymer may have a polydispersity index in the range of 1 to 6.

Any copolymer according to the invention can be used to form a biodegradable, nanoporous structure. In one form, the structure is a nerve conduit, and a wall of the nerve conduit comprises the copolymer. The structure can include pores having an average diameter in a range from 1 to 500 nanometers, or in a range from 5 to 250 nanometers, or in a range from 10 to 100 nanometers. The structure can have a porosity in a range of about 10% to about 50% or in a range of about 20% to about 40%. The structure can be a scaffold for tissue regeneration.

The invention also provides a method for forming a nanoporous structure. In the method, one prepares a copolymer including (i) at least one caprolactone unit, (ii) at least one fumarate unit, (iii) at least one third unit selected from the group consisting of acrylate units and styrenic units, and (iv) a linking moiety that forms a link between the third unit and at least one caprolactone unit or at least one fumarate unit. The linking moiety is exposed to photons thereby breaking the link and forming the nanoporous structure. The third unit can be selected from methyl methacrylate units.

The nanoporous structure can include pores having a size in a range from 10 to 100 nanometers. The linking moiety can include an alkanoyl group or an alkanedioyl group. The linking moiety can include a carbonyl group. The linking moiety can include a benzyl group. In one version of the invention, the third unit is washed away after exposing the linking moiety to photons, which may have a wavelength in the ultraviolet range. The formed nanoporous structure can have a porosity in a range of about 20% to about 40% or in a range of about 10% to about 50%.

The invention also provides a photodegradable initiator comprising a [(halo-alkylalkanoyl)oxy]-nitrobenzyl dihydroxyalkyl alkanedioate. In one non-limiting example, the [(halo-alkylalkanoyl)oxy]-nitrobenzyl dihydroxyalkyl alkanedioate is (5-[(2-bromo-2-methylpropanoyl)oxy]-2-nitrobenzyl dihydroxypropyl butanedioate).

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. The term "number average molecular weight" ($M_n$) refers to the total weight of all the molecules in a polymer sample divided by the total number of moles present ($M_n = \Sigma_i N_i M_i / \Sigma_i N_i$). Although number average molecular weight can be determined in a variety of ways, with some differences in result depending upon the method employed, it is convenient to employ gel permeation chromatography or endgroup analysis. As used herein, "weight average molecular weight" is defined as $M_w = \Sigma_i N_i M_i^2 / \Sigma_i N_i M_i$. Although weight average molecular weight ($M_w$) can be determined in a variety of ways, with some differences in result depending upon the method employed, it is convenient to employ gel permeation chromatography. As used herein, the term "polydispersity" or "polydispersity index" (PDI) refers to the ratio of a materials' "weight average molecular weight" divided by its "number average molecular weight" ($M_w/M_n$).

EXAMPLES

The following Examples have been presented in order to further illustrate the invention and are not intended to limit the invention in any way.

A. Synthesis of Poly(Caprolactone Fumarate)

A poly(caprolactone fumarate) macromer can be synthesized using the method described in Example A of U.S. Patent Application Publication No. 2007/0043202.

B. Synthesis of a PCLF-b-PMMA Copolymer

Figure 3:
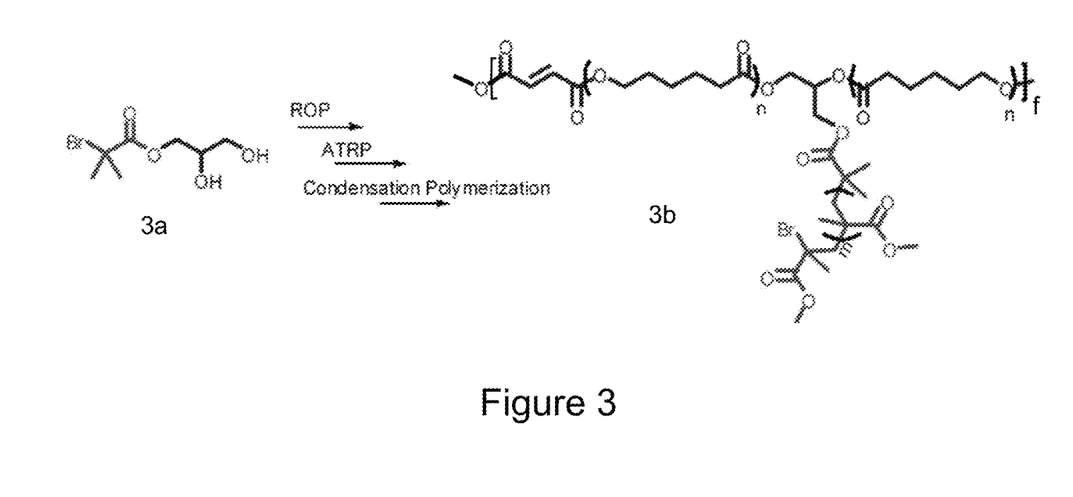
FIG. 3 shows a reaction scheme for synthesizing an example PCLF-b-PMMA copolymer according to the invention.

Looking at FIG. 3, compound 3a (2,3-dihydroxypropyl 2-bromo-2-methylpropanoate) is reacted with poly(caprolactone fumarate) and methyl methacrylate using ring opening polymerization (ROP) and/or atom transfer radical polymerization (ATRP) and/or condensation polymerization to form compound 3b (a PCLF-b-PMMA copolymer) wherein n, f, and E are integers preferably in the range of 1 to 50.

C. Synthesis of a UV Degradable Initiator

Figure 4:
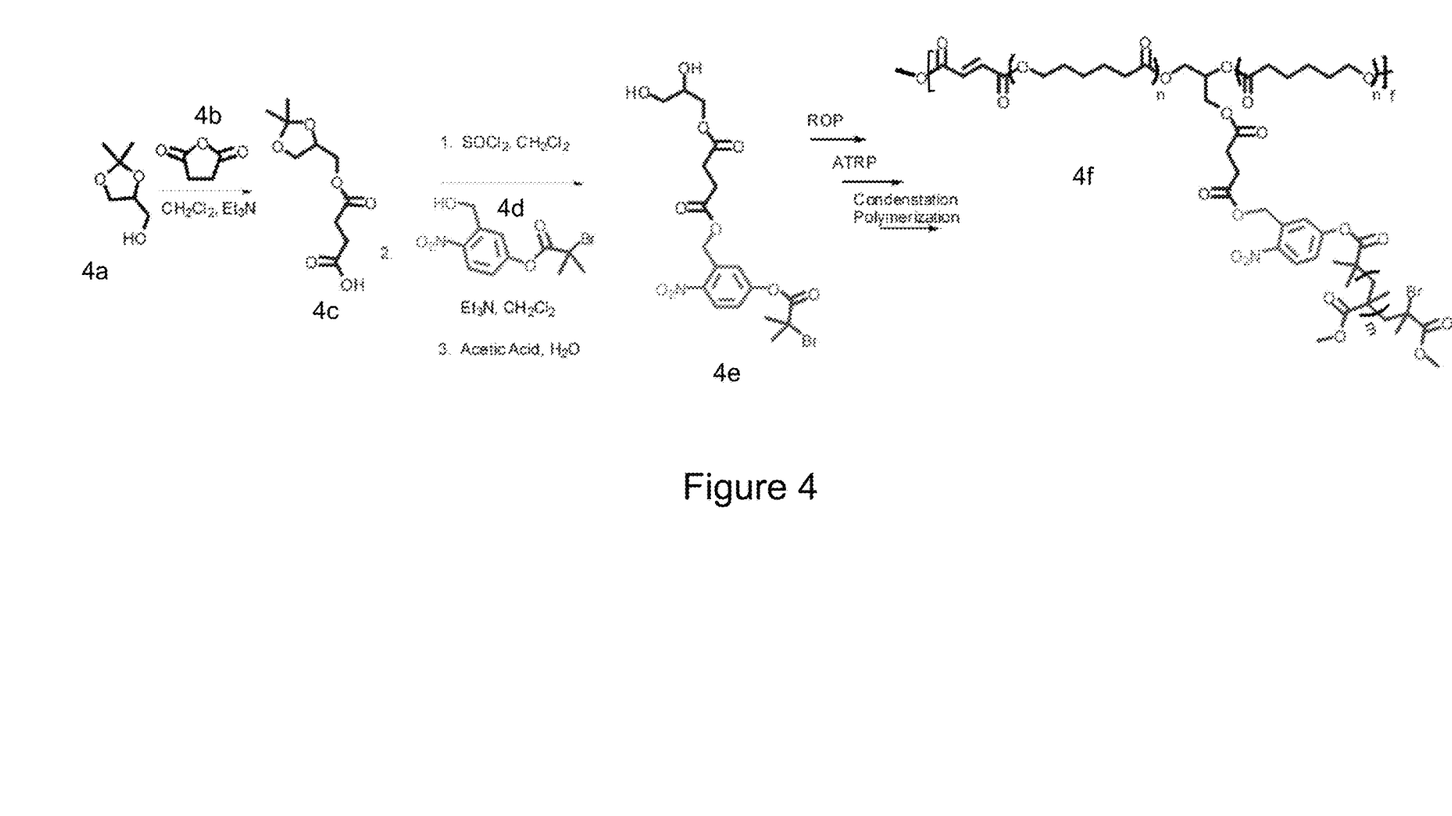
FIG. 4 shows a reaction scheme for synthesizing a UV degradable initiator according to the invention and for synthesizing another example PCLF-b-PMMA copolymer according to the invention.

Looking at FIG. 4, compound 4a ((2,2-dimethyl-1,3-dioxolan-4-yl)methanol) is reacted with compound 4b (dihydrofuran-2,5-dione) in the presence of dichloromethane and ethanolamine to produce compound 4c (4-[(2,2-dimethyl-1,3-dioxolan-4-yl)methoxy]-4-oxobutanoic acid). Compound 4c is reacted with compound 4d (3-(hydroxymethyl)-4-nitrophenyl 2-bromo-2-methylpropanoate) in the presence of sulfur oxychloride, dichloromethane and ethanolamine and washed with acetic acid and water to produce compound 4e (5-[(2-bromo-2-methylpropanoyl)oxy]-2-nitrobenzyl dihydroxypropyl butanedioate), a UV degradable initiator.

D. Synthesis of a PCLF-b-PMMA Copolymer

Still referring to FIG. 4, compound 4e is reacted with poly(caprolactone fumarate) and methyl methacrylate using ring opening polymerization (ROP) and/or atom transfer radical polymerization (ATRP) and/or condensation polymerization to form compound 4f (a PCLF-b-PMMA copolymer) wherein n, f, and E are integers preferably in the range of 1 to 50.

E. Scheme For Synthesis of a Biodegradable Nanoporous Structure

Figure 5:
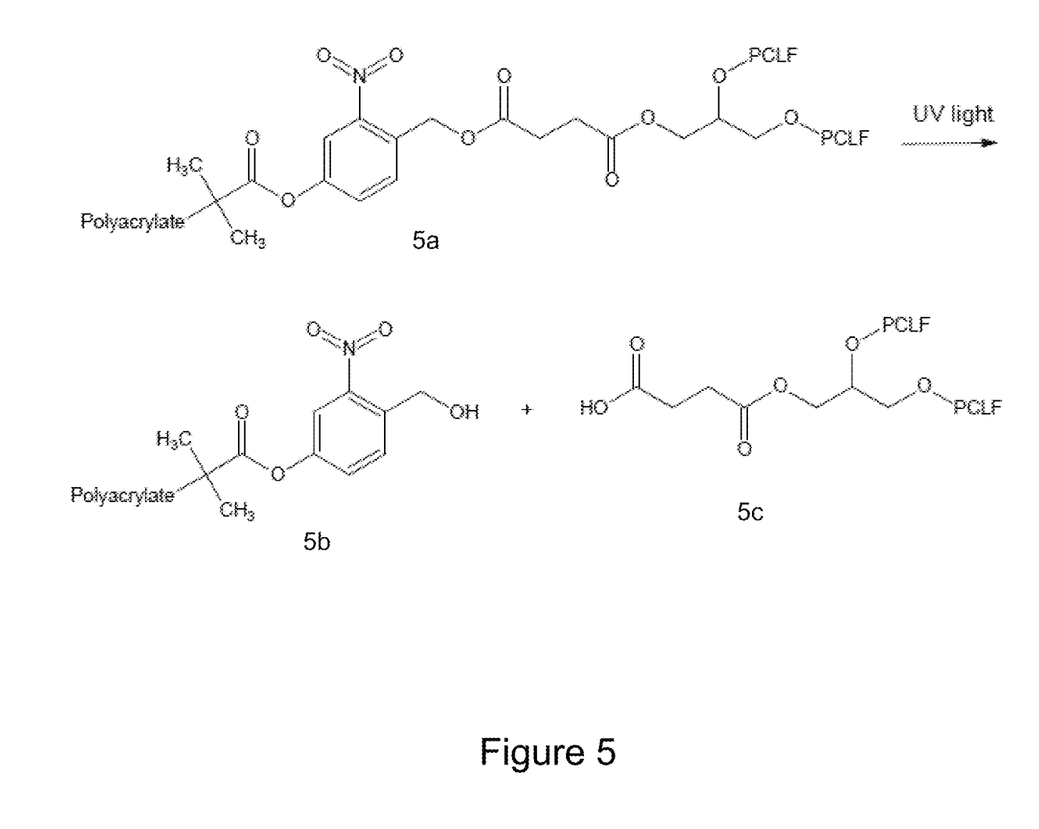
FIG. 5 shows a reaction scheme for synthesis of an example biodegradable nanoporous structure according to the invention.

Looking at FIG. 5, we have developed a block copolymer approach whereby an A-B block copolymer is connected via a photodegradable linkage (see compound 5a). After assembly into a nanostructure, the individual polymer chains can be separated by exposure to UV light. At this point, the unwanted block (compound 5b) can be washed away, and the biodegradable nanoporous structure remains (compound 5c). Compound 5c possesses a single carboxylic acid per polymer. The intramolecular rearrangement is advantageous for solid state reactions.

F. Characterization of a PCLF-b-PMMA Copolymer

The number average molecular weight ($M_n$) of a polycaprolactone (PCL) sample, a polycaprolactone-b-poly(methyl methacrylate) (PCL-b-PMMA) sample, and compound 4f (PCLF-b-PMMA) were determined by gel permeation chromatography. The composition percentage was determined by $^1$H NMR methyl vs. methylene. Table 1 shows the results below.

TABLE 1

| Polymer | $M_n$ (g mol$^{-1}$) | PCL % | PMMA % |
|---|---|---|---|
| PCL | 7500 | | |
| PCL-b-PMMA | 12500 | 67 | |
| PCLF-b-PMMA | 16000 | | 33 |

G. Characterization of Thermal Transitions and Crystalline Properties

Figure 6:
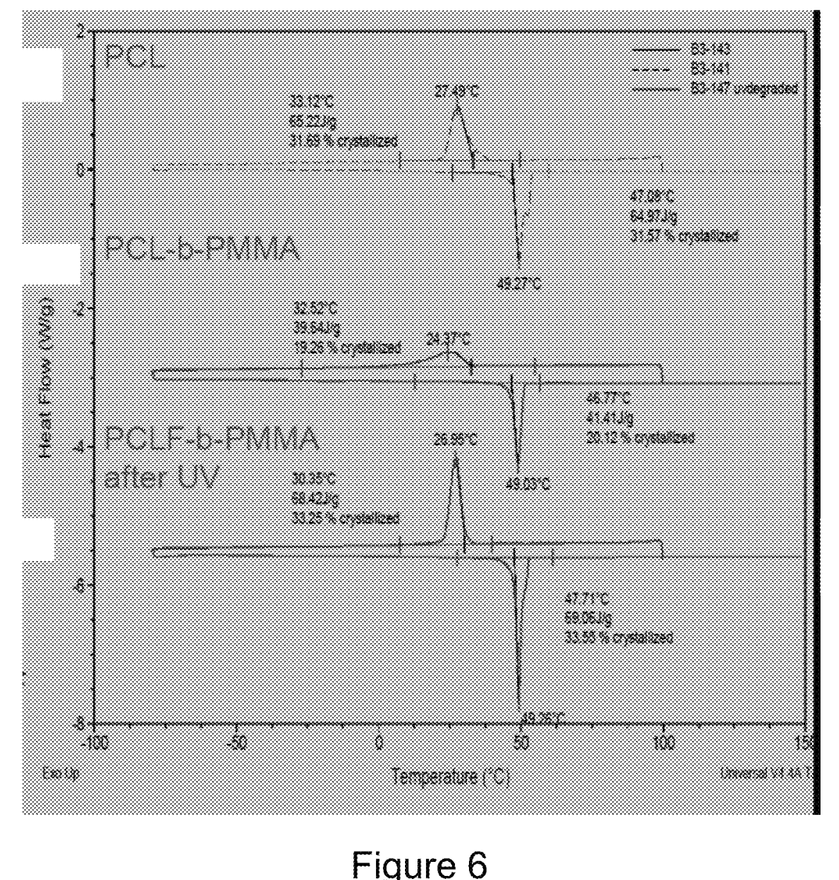
FIG. 6 shows differential scanning calorimetry results for various polymers, including an example PCLF-b-PMMA copolymer according to the invention.

In order investigate the material properties of a polycaprolactone (PCL) sample, a (PCL-b-PMMA) sample, and a PCLF-b-PMMA sample after exposure to UV light, differential scanning calorimetry experiments were performed. FIG. 6 shows that PCL is approximately 32% crystalline and has a ΔH of 66 J/g. PCL-b-PMMA shows 19% crystalline and a ΔH of 40 J/g. PCLF-b-PMMA after UV shows that the material is back to 33% crystalline and has a ΔH of 68 J/g. This indicates the material after UV degradation is mainly PCLF.

H. Transmission Electron Microscopy (TEM)

Figure 7:
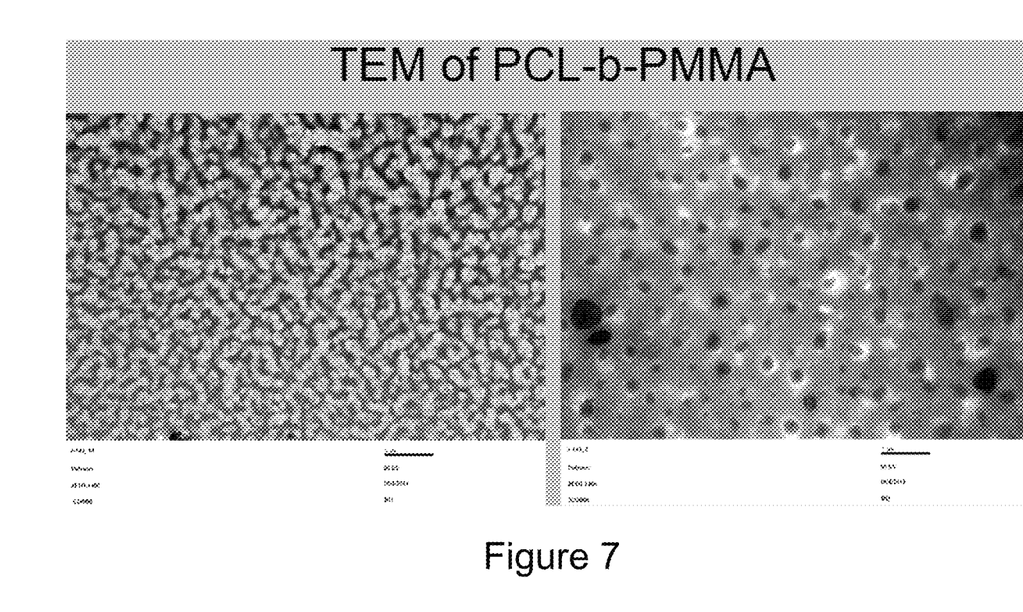
FIG. 7 shows transmission electron microscopy images of a PCL-b-PMMA film.
Figure 8:
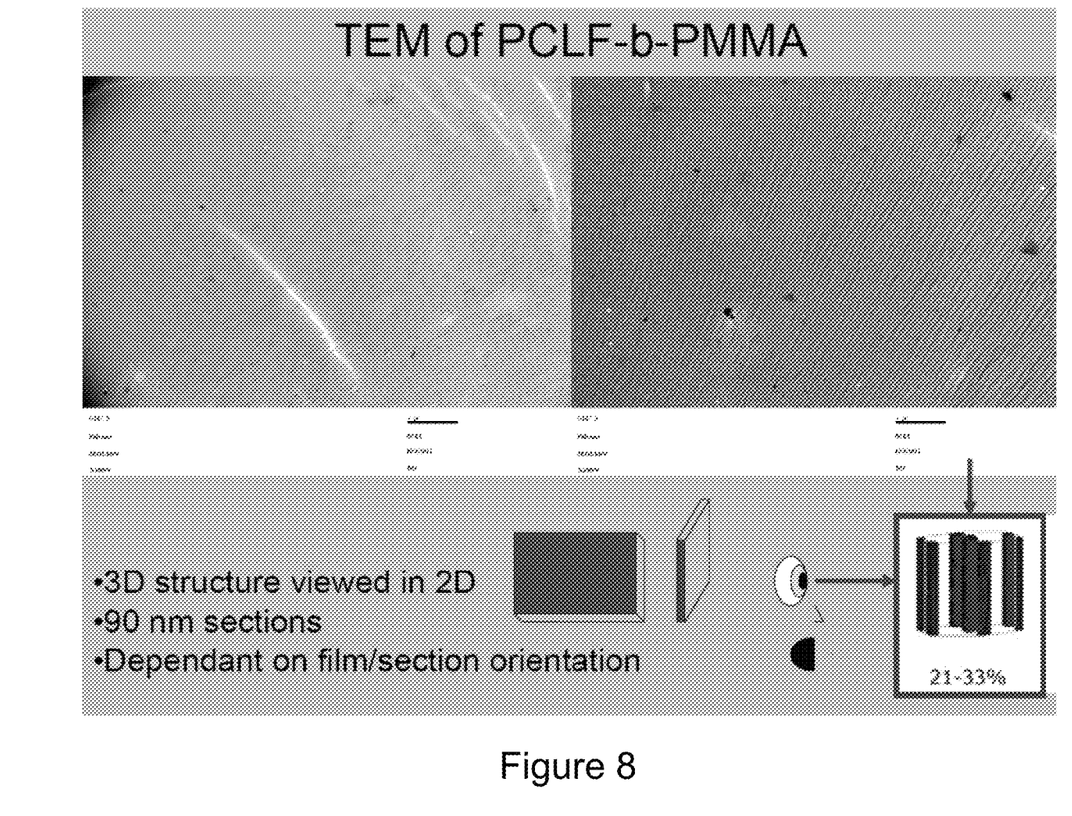
FIG. 8 shows transmission electron microscopy images of a PCLF-b-PMMA film according to the invention.

Films of PCL-b-PMMA and PCLF-b-PMMA were cast from a chloroform solvent. The nanostructure block copolymer films were cut into 90 nanometer sections, stained with $OsO_4$, and imaged using TEM. Referring to FIGS. 7 and 8, three dimensional structures were viewed in two dimensions for the 90 nanometer sections. Results were dependent on the film/section orientation. In FIG. 7, PCL-b-PMMA showed a porosity in the range 33-37%. In FIG. 8, the PCLF-b-PMMA showed a porosity in the range 21-33%.

I. UV Degradation Tests

Films of PCLF-b-PMMA were cast from a chloroform solvent. The films were irradiated with 365 nanometer light. Submersion in methanol during irradiation aided removal of poly(methyl methacrylate) (PMMA). The films turned orange in color as degradation occurred after roughly thirty minutes. Irradiation times ranged from 30 minutes to 36 hours. $^1$H NMR characterization after UV exposure showed that 80-90% of the PMMA was removed from the entire sample.

Thus, we have synthesized a UV degradable initiator that can be used to synthesize PCLF block copolymers. We have also synthesized a UV degradable poly(caprolactone fumarate)-b-poly(methyl methacrylate) block copolymer. Polycaprolactone fumarate (PCLF) was chosen as the degradable polymer of choice to create a nanoporous scaffold for nerve conduit applications. We have assembled this block copolymer into nanostructured materials which were imaged using transmission electron microscopy. We have further showed that we can degrade this material and selectively remove 90% of the poly(methyl methacrylate) block as shown by $^1$H NMR. We have also shown that poly(methyl methacrylate) (PMMA) is mostly removed by differential scanning calorimetry. Although we have made a PCLF-b-PMMA block copolymer, PMMA can be substituted with any acrylate or styrene with no changes. Additionally, the initiator and block copolymer design can be altered to incorporate different initiators for other polymer systems.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A copolymer having structure (I):

wherein n, f, and E are integers.

2. The copolymer of claim 1 wherein:

n, f, and E are integers in a range of 1 to 50.

3. The copolymer of claim 1 wherein:

the copolymer has a number average molecular weight in the range of 3000 to 60,000 g mol$^{-1}$.

4. The copolymer of claim 1 wherein:

the copolymer has a number average molecular weight in the range of 10,000 to 20,000 g mol$^{-1}$.

5. The copolymer of claim 1 wherein:

the copolymer has a polydispersity index in the range of 1 to 6.

6. A copolymer having structure (II):

wherein n, f, and E are integers.

7. The copolymer of claim 6 wherein:
n, f, and E are integers in a range of 1 to 50.

8. The copolymer of claim 6 wherein:
the copolymer has a number average molecular weight in the range of 3000 to 60,000 g mol$^{-1}$.

9. The copolymer of claim 6 wherein:
the copolymer has a number average molecular weight in the range of 10,000 to 20,000 g mol$^{-1}$.

10. The copolymer of claim 6 wherein:
the copolymer has a polydispersity index in the range of 1 to 6.

11. A nerve conduit comprising:
a wall comprising the copolymer of claim 1,
wherein the wall is biodegradable and nanoporous.

12. The nerve conduit of claim 11 wherein:
the wall includes pores having a size in a range from 1 to 500 nanometers, and
the wall has a porosity in a range of about 20% to about 40%.

13. A nerve conduit comprising:
a wall comprising the copolymer of claim 6.

14. The nerve conduit of claim 13 wherein:
the wall includes pores having a size in a range from 1 to 500 nanometers, and
the wall has a porosity in a range of about 20% to about 40%.

* * * * *